United States Patent [19]
Plotkin

[11] 3,959,466
[45] May 25, 1976

[54] HIGHLY ATTENUATED CYTOMEGALOVIRUS VACCINE AND PRODUCTION THEREOF

[75] Inventor: Stanley A. Plotkin, Philadelphia, Pa.

[73] Assignee: The Wistar Institute, Philadelphia, Pa.

[22] Filed: Apr. 15, 1974

[21] Appl. No.: 460,951

[52] U.S. Cl................................. 424/89; 195/1.3
[51] Int. Cl.² .................... A61K 39/12; C12K 5/00
[58] Field of Search........................ 424/89; 195/1.3

[56] References Cited
OTHER PUBLICATIONS

Elek, et al., *The Lancet*, Jan. 5, 1974, pp. 1–5.

Chambers, et al., *Applied Microbiology*, Vol. 22, pp. 914–918, Nov. 1971.

*Primary Examiner*—Sam Rosen
*Attorney, Agent, or Firm*—Howson and Howson

[57] ABSTRACT

A cytomegalovirus (CMV) vaccine, capable of inducing immunity in humans against cytomegalic inclusion disease (CID), without spread to contacts and with minimal excretion of the virus, is prepared by serially passaging virulent CMV in human diploid lung fibroblasts.

8 Claims, No Drawings

HIGHLY ATTENUATED CYTOMEGALOVIRUS VACCINE AND PRODUCTION THEREOF

BACKGROUND OF THE INVENTION

Cytomegalovirus (CMV) infection in utero is an important cause of central nervous system damage in newborns. Although the virus is widely distributed in the population, about 40% of women enter pregnancy without antibodies and thus are susceptible to infection. About 1% of these women undergo primary infection in utero. Classical cytomegalic inclusion disease is rare; however, a proportion of the infected infants, including those who were symptom free, are subsequently found to be mentally retarded (Lancet Jan. 5, 1974, pp. 1–5).

Preliminary estimates based on surveys of approximately 4,000 newborns from several geographical areas indicate that the virus causes significant damage of the central nervous system leading to mental deficiency in at least 10%, and perhaps as high as 25%, of infected infants. Assuming that about 1% of newborn infants per year excrete CMV and that about one fourth of those develop mental deficiency, in the United States this means approximately 10,000 brain-damaged children born per year. This is a formidable number, particularly in view of the ability of these children to survive (J. of Infect. Dis. 123, No. 5, 555 (May 1971)).

In view of the seriousness of the problem, research directed toward the development of an effective CMV vaccine has been stimulated in recent years. The problem for vaccination is to provide cell-mediated and humoral immunity without allowing spread of virus throughout the body of the vaccinee and without causing ill effects. The vaccine should be useful in protecting women against infection during pregnancy. Vaccination of adolescent girls should reduce the incidence of primary CMV infection in pregnancy and eliminate fetal brain damage due to this cause.

DESCRIPTION OF THE INVENTION

The present invention provides a vaccine which is capable of inducing immunity against CMV and thus is useful in protecting women against infection during pregnancy, whereby damage to the central nervous system, including mental retardation, of newborns may be greatly reduced. The vaccine of this invention advantageously does not evidence spread of the virus to contacts. Furthermore, the vaccine, by reason of its mode of preparation, does not possess the capability of transmitting latent animal virus to vaccinees. The invention also consists in a novel process for preparing the vaccine.

The vaccine of the present invention possess the above-described advantages by virtue of its mode of preparation. An essential feature of the process for the preparation of the vaccine is the serial passaging of CMV in human diploid lung fibroblasts, particularly WI-38 and MRC-5 fibroblasts, preferably the former.

The WI-38 fibroblasts were originally derived from a single human lung; they are pedigreed in the sense that they have been extensively characterized biologically, biochemically, virologically, and genetically. The MRC-5 fibroblasts were similarly derived from a single human lung, but of a different individual, and have been pedigreed in like manner. These two cell lines are standardized, in contrast to conventionally used primary animal cells. WI-38 has been described in Exper. Cell Res. 25, 585 (1961) and has been deposited with the American Type Culture Collection and assigned the designation ATCC CCL-75. MRC-5 has been described in Nature 227 168 (July 11, 1970). WI-38 has been made available to laboratories and may be obtained from the collection. The use of these cell lines for the propagation of the virus minimizes the likelihood of latent animal viruses being transmitted to a vaccinee by means of the vaccine.

The Towne strain of CMV, a preferred strain for use in preparation of the vaccine because of its broad antigenic spectrum, was isolated from the urine of a two month old male infant with cytomegalic inclusion disease (symptoms - central nervous system damage and hepatosplenomegaly). This strain of CMV was isolated by Stanley A. Plotkin, M.D. of the Wistar Institute of Anatomy and Biology, Philadelphia, Pa., and is described in J. Virol. 11 No. 6, 991 (June 1973). However, other strains of CMV may be used.

Propagation of the human diploid lung fibroblasts may be carried out by any of the standard methods described in the literature. Specific examples of such propagation techniques are disclosed in Exper. Cell Res. 25, 585 (1961), and Virology 16, 147 (1962). The tissue culture system comprises Eagle's basal medium (BME) or Eagle's minimal essential medium (MEM) in Eagle's balanced salt solution supplemented with pre-screened calf serum containing a sterilizing amount of an antibiotic such as penicillin, streptomycin, chlortetracyline, or other antibiotic, or mixtures thereof, the system being buffered at a pH of about 6.8 – 8.5 with a conventional biological buffering agent such as an alkali metal bicarbonate, carbonate or hydrogen phosphate.

The CMV is cultivated for vaccine use by inoculating human diploid lung fibroblasts with CMV. Urine containing CMV is a particularly useful starting material for inoculating the fibroblasts. The trypsinized infected cells are harvested and serially passaged in human diploid lung fibroblasts. Each incubation proceeds for a period of 7 days and is conducted at a temperature of about 37°C. The number of passages is such as to produce first a strain of CMV which releases large amounts of cell-free virus, followed by attenuation of the cell-free virus. At least about 50 and preferably about 125 to 150 total passages are used. The attenuated virus is then harvested and subjected to standard sterility tests for the presence of bacteria, fungi, mycoplasma, and other contaminating agents.

The term "attenuated virus" as employed herein refers to a virus of which the virulence has been altered by the method of culture so that it does not produce severe symptoms when inoculated into humans although retaining its antigenicity, that is, its ability to stimulate production of antibodies.

The attenuated virus is utilized as a vaccine by filtering the harvested material in order to remove cells or bacteria, and the filtrate is either used as is, frozen for later use, or lyophilized and subsequently reconstituted with a solvent such as water. Preferably a stabilizer such as albumen is used where the filtrate is lyophilized. The vaccine may be administered subcutaneously. The dosage which may be used is a minimum of 100 $TCID_{50}$ of attenuated CMV, and may be as high as 10,000 $TCID_{50}$.

The attenuated virus may be produced in larger quantities by inoculating human diploid lung fibroblasts with the virus, and growing the attenuated virus therein. The attenuated virus may be harvested at the time of maximum titer, e.g. about one week.

The following description of the preparation and testing of the CMV vaccine is intended to illustrate the invention, but is not to be construed as limiting its scope.

PROCEDURE FOR OBTAINING VIRUS

The CMV used is obtained from the urine of a two month old male human infant with cytomegalic inclusion disease. This strain is designated Towne and has been described hereinabove. The urine is inoculated onto WI-38 human diploid lung fibroblasts. The nutrient medium used for tissue culture of the virus is Eagle's minimal essential medium (MEM) with 2% of pre-screened calf serum added. The concentration of antibiotics in each ml. of medium is 100 $\mu$g of penicillin, 10 $\mu$g of gentamicin, and 2 $\mu$g of amphotericin-B. Other antibiotics may be used in place of those specifically enumerated above.

PROCEDURE FOR PREPARING ATTENUATED CMV

The harvest comprising supernatant fluid, and virus infected cells removed from the surface of the vessels using 0.25% trypsin in a physiological saline solution is inoculated on stationary WI-38 human diploid lung fibroblasts to initiate infection of these cells and then subsequently passaged. The nutrient medium used to initiate cell infection and in all subsequent passages is the same as that employed for tissue culture of the virus, described above. The temperature used in each passage is 37°C. However, temperatures somewhat below this temperature, e.g. temperatures in the range of about 30° to 37°C. can also be used. The duration of each passage is seven days, but passages of a somewhat shorter or longer period, e.g. 5 or 10 days, may be used.

In the initial passages, which are about 10 in number, supernatant fluid containing virus infected cells harvested from each previous passage is passaged on fresh WI-38 human diploid lung fibroblasts. Approximately 25% of cell-containing fluid from a preceeding passage is used in each passage. The number of passages selected is such as to obtain a strain which produces a substantial amount of cell-free virus, CMV ordinarily being cell associated. Thus, a somewhat smaller or greater number of passages may be used.

The supernatant fluid from the tenth passage is obtained by decanting and is centrifuged at 1,200 rpm to obtain a fluid containing cell-free virus. The cell-free fluid containing cell-free virus is then serially passaged 28 times on fresh WI-38 human diploid lung fibroblasts, 1 ml. of fluid being used to inoculate vessels each having a surface area of 75 cm$^2$. Although 28 passages are used, the number of passages need merely be sufficient to provide the desired amount of cell-free CMV. Thus, a greater or lesser number of passages of the cell-free fluid could be used.

The supernatant fluid, which may also contain virus released from cells by sonication, is harvested and then serially passaged on fresh WI-38 a sufficient number of times, e.g. about 115 times, to attenuate the virus. The total number of passages used in the overall process hereinabove described will ordinarily be between about 50 and 150, preferably about 125 to 150.

Cloning of the attenuated virus by terminal dilution is performed at 50, 60 and 70 passages.

The virus for vaccine pools is harvested from the supernatant fluids of infected WI-38 cultures at the time of maximum virus titer, generally about one week. By this procedure a larger amount of attenuated CMV is obtained from that initially prepared.

CHARACTERISTICS OF THE CMV VACCINE

The CMV vaccine grows on human fibroblasts such as WI-38 cells. Its cytopathic effect is characteristic of human CMV described in the literature. It can be readily propagated in cell-free form by filtering the supernatant of infected culture (3 micron filter) and inoculating on fresh WI-38 cells. CPE occurs within 4 – 10 days depending on the multiplicity of infection. Inclusion bodies form as described in the literature and can be stained with Haematoxylin-Eosin or Giemsa. The attenuated virus forms plaques with a nutrient agarose overlay.

The vaccine should be stored at −70°C. in a solution of 70% sorbitol in distilled water (one volume of virus to one volume of sorbitol solution).

The cell-free attenuated virus can be seroneutralized with commercially available human antiserum (Flow Labs., Bethesda, Md.), CF titre 1:16 (diluted 1:10). 0.1 ml. diluted serum neutralizes 250 TCID$_{50}$. Hyperimmune guineapig serum against AD 169 strain may also be used.

The following table summarizes the serum neutralization (SN) titres alone and in the presence of complement. SN was done in microplaques (Linbro): 0.025 ml. of suspension of 60 TCID$_{50}$ Towne 125 plus 0.025 ml. diluted serum. After one hour 0.250 ml. containing 10$^4$ WI-38 cells in Eagle's modified basal medium with 10% unheated calf serum is added. Microplaques are read after 5 – 7 days' incubation at 37°C. Eight wells per dilution were used.

| Serum Sample | Neutralization | |
|---|---|---|
| | Alone | with C' |
| Rabbit No. 1 | 8 | 8 |
| No. 2 | 8 | 64 |
| No. 3 | 8 | 32 |
| No. 4 | 8 | 64 |
| Guinea Pig | 20–100 | 100 |
| Human Antiserum | 40 | 40 |

PROCEDURE FOR TESTING VACCINE

Each pool used for inoculation was subjected to tests for the presence of bacteria, fungi, and mycoplasma by inoculation onto appropriate artificial media. Tests for safety in animals included injection of aliquots of the pool into adult mice (intraperitoneally and intracerebrally), suckling mice (intraperitoneally and intracerebrally), guinea pigs (intraperitoneally), and rabbits (intradermally). Examination of the animals at different periods of time (all several weeks) after inoculation, revealed that all of the animals remained well.

Twenty cercopithecus monkeys were inoculated with the vaccine, 0.5 ml. intraspinally, intracerebrally, respectively, and 1 ml. intramuscularly. They were all seronegative to 100 TCID$_{50}$ CMV neutralization, both in the presence and absence of fresh guinea pig complement. The monkeys were tested again three weeks later. No seroconversion was demonstrated by the same monkeys upon clinical or pathological examination, during this period of observation.

Further tests for identity and for the absence of contaminating agents were performed in tissue culture. Primary African green monkey kidney, human embryo kidney, primary rabbit kidney, and WI-38 cells all were inoculated with aliquots of virus either directly or after neutralization for 1 hour at 37°C. with rabbit CMV serum. There was no evidence of any agent other than CMV vaccine in the pool. Titration of pools for quantity of CMV virus was performed by end point dilution assay on WI-38 cells.

RESULTS OF TESTING VACCINE IN HUMANS

The vaccine was tested on adults, pretested for antibody to CMV and only seronegatives were included in the tests. Ten seronegative adults were given $10^{3.0}$ $TCID_{50}$ intranasally. There were no seroconversions, demonstrating that the virus was no longer infectious by the usual route. Nine other adults were given the same dose subcutaneously, and there was seroconversion in all cases. No symptoms were observed, nor was virus recovered from urine, throat or blood.

In obtaining the aforesaid results, the viruses were inoculated in a volume of 1 ml. subcutaneously. Throat swabs were made with cotton-tipped applicator sticks moved over the posterior pharynx. Both types of swabs were placed immediately in screwcap tubes containing Hanks' medium with 0.1 percent gelatin, 1000 $\mu$g of streptomycin and 400 $\mu$g of mycostatin per ml. The specimens either were stored at 4°C. until inoculated into tissue cultures on the same day, or at −20°C. until tested within two weeks. Urine was inoculated directly on WI-38 cells. Tests for viremia were performed by collecting heparinized blood and allowing it to settle by gravity at 4°C. until leucocyte-rich plasma was obtained. After sonication for two minutes, the plasma was inoculated into tissue culture. Antibody studies were done on serum from clotted blood specimens using complement-fixation and fluorescent antibody tests.

In a subsequent test nine new seronegative adults were given the same dose ($10^{3.0}$ $TCID_{50}$) subcutaneously. No systemic symptoms were observed and all nine developed antibodies to CMV.

What is claimed is:

1. A process for preparing an attenuated cytomegalovirus vaccine comprising serially passaging in WI-38 human diploid lung fibroblasts a strain of cytomegalovirus having a broad antigenic spectrum a sufficient number of times to obtain a strain of cytomegalovrius which produces a substantial amount of cell-free cytomegalovirus, and serially passaging said cell-free cytomegalovirus in WI-38 human diploid lung fibroblasts a sufficient number of times so that the virus, when administered to humans, induces immunity without producing severe symptoms or more than minimal virus excretion and spread to contacts, the total number of passages employed in preparing said vaccine being from about 50 to about 150.

2. A process for preparing an attenuated cytomegalovirus vaccine comprising growing said attenuated cytomegalovirus of claim 1 in WI-38 human diploid lung fibroblasts for a sufficient length of time to produce a larger amount of said attenuated virus and harvesting the resulting attenuated virus.

3. A process according to claim 1 in which the passages are carried out at a temperature of 30° to 37°C. for 5 to 10 days.

4. A process according to claim 3 in which the total number of passages is about 125 to 150.

5. A process according to claim 4 in which trypsinized cells infected with cytomegalovirus are passaged 10 times on fresh human diploid lung fibroblast cells, followed by subsequent viral passaging of cell-free virus on fresh human diploid lung fibroblast cells.

6. A cytomegalovirus vaccine comprising an attenuated cytomegalovirus prepared by growing said attenuated cytomegalovirus of claim 1 in WI-38 human diploid lung fibroblasts for a sufficient length of time to produce a larger amount of said attenuated virus and harvesting the resulting attenuated virus.

7. A process for immunizing humans against disease caused by cytomegalovirus comprising subcutaneously administering to humans at least an immunizing effective amount of attenuated cytomegalovirus vaccine of claim 6.

8. Cytomegalovirus vaccine comprising a carrier and an effective amount of attenuated cytomegalovirus prepared by serially passaging in WI-38 human diploid lung fibroblasts a strain of cytomegalovirus having a broad antigentic spectrum a sufficient number of times to obtain a strain of cytomegalovirus which produces a substantial amount of cell-free cytomegalovirus, and serially passaging said cell-free cytomeglovirus in WI-38 human diploid lung fibroblasts a sufficient number of times so that the virus, when administered to humans, induces immunity without producing severe symptoms or more than minimal virus excretion and spread to contacts, the total number of passages employed in preparing said vaccine being from about 50 to about 150.

* * * * *